(12) United States Patent
Fiorini-Puybaret

(10) Patent No.: US 11,311,591 B2
(45) Date of Patent: Apr. 26, 2022

(54) USE OF COPAIFERA OLEORESIN IN PATHOLOGIES OF THE PROSTATE

(71) Applicant: PIERRE FABRE MEDICAMENT, Boulogne-Billancourt (FR)

(72) Inventor: Christel Fiorini-Puybaret, Toulouse (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 0 days.

(21) Appl. No.: 16/495,771

(22) PCT Filed: Mar. 20, 2018

(86) PCT No.: PCT/EP2018/057076
§ 371 (c)(1),
(2) Date: Sep. 19, 2019

(87) PCT Pub. No.: WO2018/172380
PCT Pub. Date: Sep. 27, 2018

(65) Prior Publication Data
US 2020/0093879 A1    Mar. 26, 2020

(30) Foreign Application Priority Data
Mar. 20, 2017  (FR) ..................... 1752284

(51) Int. Cl.
| | | |
|---|---|---|
| *A61K 36/00* | (2006.01) |
| *A61K 36/48* | (2006.01) |
| *A61P 13/08* | (2006.01) |
| *A61K 31/19* | (2006.01) |
| *A61K 31/194* | (2006.01) |
| *A61K 31/341* | (2006.01) |

(52) U.S. Cl.
CPC .............. *A61K 36/48* (2013.01); *A61K 31/19* (2013.01); *A61K 31/194* (2013.01); *A61K 31/341* (2013.01); *A61P 13/08* (2018.01)

(58) Field of Classification Search
CPC ..................................................... A61K 36/00
USPC ......................................................... 424/725
See application file for complete search history.

(56) References Cited

PUBLICATIONS

Gomes et al., "Antineoplasio Activity of Copailera Muitijuga Oil and Fractions Against Ascitic and Solid Ehrlich Tumor," Medicinal & Aromatic Plants Abstracts Scientific Publishers. vol. 31, No. 4, Aug. 2009, 1 page, XP018025483, abstract only.
Lama et al., "Bioassay Guided Identification of Small Chaperone Proteins α-crystallin and Hsp27 Inhibitors from Copaiba Oil," Phytochemistry Letters, vol. 10,2014 (Available online Aug. 17, 2014), pp. 65-75, XP0055422813.
Leandro et al., "Chemistry and Biological Activities of Terpenoids from Copaiba (*Copaifera* spp.) Oleoresins", Molecules, vol. 17, No. 12, 2012 (Published Mar. 30, 2012), pp. 3866-3889, XP055313075.
Rittmaster, "5α-Reductase Inhibitors," Journal of Andrology vol. 18. No. 6, Nov. /Dec. 1997, pp. 582-587.
Viega et al., "Chemical Composition and Anti-inflammatory Activity of Copaiba Oils from Copaifera cearensis Huber ex Ducke, Copaifera reticulata Ducke and Copaifera . . . ," Journal of Ethnopharmacology, vol. 112, No. 2, 2007 (Available online Mar. 7, 2007), pp. 248-254, XP022085297.

*Primary Examiner* — Michael V Meller
(74) *Attorney, Agent, or Firm* — Birch, Stewart, Kolasch & Birch, LLP

(57) ABSTRACT

The invention relates to a use of *Copaifera oleoresin* for producing a medicament for preventing and/or treating pathologies of the prostate, particularly benign prostatic hyperplasia and/or prostate cancer.

6 Claims, No Drawings

USE OF COPAIFERA OLEORESIN IN PATHOLOGIES OF THE PROSTATE

The present invention relates to the use of *Copaifera oleoresin* to prevent and/or treat prostate diseases, in particular benign prostatic hyperplasia and/or prostate cancer.

The genus *Copaifera* includes 35 species, all of which are trees from tropical America, i.e. Mexico, northern Argentina and mainly Brazil. In this territory there are more than 20 species, the most abundant being *C. officinalis, C. reticulata, C. multijuga*. *Copaifera officinalis* is a tree found mainly in Brazil, Colombia and Venezuela. It has reddish-brown wood and grows to 25 m. The leaves are composed, paripinnate with 2 to 10 leaflets, alternate or sub-opposite, apiculate and unevenly rounded at the base. They are 3-8 cm long and 2-4 cm wide. The white flowers, generally sessile, are grouped into inflorescences of 7-14 cm. The fruits are small pods swollen at maturity with a diameter of 20-25 mm, glabrous, apiculate containing an ovoid seed.

Oleoresin is a substance obtained by incising the bark of several *Copaifera* species. Located in anastomosed secretory channels of the secondary wood and the marrow, its extraction therefore requires very deep incisions of the trunk which allows it to flow naturally from the tree.

After steam distillation or hydrodistillation, the oleoresin makes it possible to obtain Copaiba essential oil, famous in perfumery.

Copaiba oleoresin has been used in medicine since the 16th century by the indigenous people of Brazil. It has a long history of use in traditional Brazilian medicine, to treat wounds and remove scars, as febrifuge, urinary tract antiseptic, against leukorrhea and gonorrhoea. Considered a general tonic, its indications were as follows: venereal disease, respiratory disease, asthma, rheumatism, secondary skin lesions, ulcers. At low doses, it is a stimulant with direct action on the stomach. Copaiba oleoresin reduces excessive mucus secretion caused by inflammation. Today, Copaiba oleoresin is sold in capsules in pharmacies in Brazil where it is indicated for all types of internal inflammation and stomach ulcers. When applied locally, it is a powerful antiseptic and anti-inflammatory healing agent, it helps to heal the most difficult wounds. Copaiba oleoresin is said to be very effective on joint pain, benign sprains, hematomas, tendonitis. Oleoresin is applied directly to the skin. Oleoresin is also used as a massage oil for painful or inflamed muscles and joints.

The prior art discloses that chaperone proteins (such as HSP27) contribute to a resistance to chemotherapy by chemical agents in cancerous tissues and it is thus described that hardwickiic acid from *Copaifera* oil inhibits HSP27. Research on this topic aims to identify other chaperone inhibitors in *Copaifera* oil (Phytochemistry Letters, 10 (2014); 65-75). One such document indicates that the non-acidic fraction and only one acidic subfraction (without diterpenic acids or diterpenic acid esters) of the oil have antiproliferative activity. The other sub-fractions (i.e. acidic) show anti-chaperone activity. This document thus targets a very specific case, namely a combination of *Copaifera* oil with a chemotherapeutic treatment by chemical agent in order to counter the resistance of cancer cells to said chemical agent treatment. This document concludes only that the hardwickiic acid from *Copaifera* oil is active in combination with an antineoplastic agent, which is the anticancer agent, to inhibit chaperone proteins that represent agents contributing to resistance to said anticancer agent.

Copaiba oleoresin, optionally distilled, is also used in cosmetics, in the manufacture of soaps, bubble baths, detergents and creams, and as a fixative in perfumery. Oleoresin is sometimes used as a flavouring agent in the food industry. Copaiba oleoresin is also used as material for artists, particularly in oil paint recipes and in decorative ceramics.

Oleoresin is a colourless and thin liquid which acquires an oleaginous consistency and a greenish-yellow colour over time. Its consistency and colour vary slightly, depending on the tree from which it comes and on the essential oil found there. Its smell is strong and unpleasant, its flavour is bitter and pungent. Oleoresin is insoluble in water, totally soluble in alcohol and in ether The oleoresin of *C. officinalis* consists of two fractions which are distinguished by their volatility; each of the fractions being characterized by distinct chemical compounds:

A "volatile" essential oil representing 50-90% of the oleoresin, which is mainly composed of sesquiterpenes. Among these sesquiterpenes, mainly germacrene D, (E)-β-caryophyllene, β- and δ-elemene, α-ylangene, α-gurjunene, α-humulene can be distinguished. The minority sesquiterpenes are α-cubebene, α-copaene, 7-epi-sesquithujene, cis- and trans-α-bergamotene, sesquisabinene-A and -B, 4αH, 10αH-guaia-1(5),6-diene, allo-aromadendrene, γ-uurolene, α-amorphene, β-selinene, bicycliosesquiphyllandrene, α-muurolene, β-bisabolene, γ-cadinene, δ-cadinene, cis-calamene, zonarene, cakina-1'4-diene, α-cadinene, α-calacorene, selina-3,7(11)-diene, germacrene B. This volatile oil is very clear, colourless, with a very pronounced smell and taste.

A "non-volatile" fraction representing 10-50% of the oleoresin, which is composed mainly of the following diterpenic acids and/or diterpenic acid esters: copalic acid, copaiferolic acid, agathendioic acid dimethyl ester, agathic acid, 3β-hydroxyanticopalic acid methyl ester, hardwickiic acid, 7α-acetoxyhardwickiic acid. This distillation residue is a viscous liquid with an aromatic odour and a dark brown colour.

Surprisingly, the inventors have shown that *Copaifera* oleoresin has a particularly advantageous anti-5α-reductase activity.

The role of 5α-reductase inhibitors is established in prostate pathophysiology (Rittmaster, Journal of Andrology, vol. 18, no. 6, 1997), particularly in benign prostatic hyperplasia and prostate cancer.

The prostate is the largest exocrine gland in the male urogenital system. It is located at the intersection of the genital and urinary tracts. Along with seminal vesicles, the prostate plays an essential role in the synthesis and release of sperm fluid. It contributes more indirectly to the micturition-continence cycle through its smooth muscle component. Finally, the prostate is surrounded by vascular and nerve pedicles involved in the male sexual response. With age, anatomical changes in the prostate gland can sometimes be the cause of urinary disorders and sexual dysfunctions that lead to a decrease in quality of life.

The prostate can be the site of three major diseases, prostatitis, prostate adenoma or benign prostatic hyperplasia, and prostate cancer. However, to date, the enzyme 5α-reductase is only involved in benign prostatic hyperplasia and prostate cancer.

Benign prostatic hyperplasia is a common condition promoted by aging and related to the development of a prostate adenoma responsible for a chronic obstruction to bladder emptying. Benign prostatic hyperplasia is characterized by an increase in the size of the prostate gland. A large prostate compresses the urethra while pressing on the bladder, resulting in a frequent need to urinate and various problems with urination, lower and intermittent flow, pain, etc. Almost all men are prone to benign prostatic hyperplasia as they age. Indeed, more than 50% of men aged 60 have it, and 90% of those over age 80. However, not all of them suffer from it, as one in two men is bothered by urinary symptoms. The causes of this condition are not clearly established, there is probably a hereditary predisposition, but other factors come into play. However, this condition is not to be taken lightly, as there are several possible complications such as urinary tract infections, acute urine retention, bladder stones and kidney damage.

Prostate cancer is a common disease that is the second most common male cancer in industrialized countries. There would be a genetic predisposition. Most prostate cancers progress very slowly. Often the tumour remains localized in the prostate gland and has limited health effects, sometimes causing urinary or erectile dysfunction. However, some prostate cancers may progress and spread more quickly. Adenocarcinoma is the most common form of prostate cancer. It represents about 95% of cases. The severity of the cancer depends on the extent of the tumour and the type of cancer cells.

Testosterone promotes prostate growth through one of its metabolites, dihydrotestosterone. Testosterone is transformed into dihydrotestosterone by the action of 5α-reductase. Dihydrotestosterone has a high binding affinity for the androgen receptor. Compared to testosterone, dihydrotestosterone stimulates by a factor of 2 to 10 the transcriptional activity of prostate cells. Ex vivo, dihydrotestosterone has a much more powerful stimulating effect on prostate tumour growth than testosterone. In men with symptomatic benign prostatic hyperplasia, 5α-reductase inhibition decreases prostate volume, improves symptoms and urinary output, and reduces the risk of acute urinary retention.

There are two isoforms of 5α-reductase, 5αR1 and 5αR2, which are encoded respectively by two distinct genes, SRD5A1 and SRD5A2, located on separate chromosomes. The 5αR2 isozyme occurs mainly in male reproductive tissues, seminal vesicles, epididymis and prostate. While 5αR1 isozyme is detected mainly in the liver and skin. 5αR2 is present in high concentrations in prostate tissue and has a high affinity for testosterone. Finasteride is a potent 5αR2 inhibitor, with a half maximal inhibitory concentration ($IC_{50}$) of 69 nM but which is much less effective at inhibiting 5αR1, $IC_{50}$ of 360 nM. In contrast, dutasteride similarly inhibits both 5αR1 and 5αR2, $IC_{50}$ of 6 nM and 7 nM, respectively. Dutasteride appears to be more effective than finasteride, respectively 94.7% vs 70.8% in reducing mean serum dihydrotestosterone levels. Intraprostatically, a greater reduction in dihydrotestosterone was observed with dutasteride, suggesting that 5αR1 appears to contribute to the synthesis of intraprostatic dihydrotestosterone. The role of 5α-reductase in the inhibition of prostate cancer has been reported in animal models.

According to a first embodiment, the invention concerns a *Copaifera* oleoresin for use as a medicinal product intended for the treatment and/or prevention of benign prostatic hyperplasia and/or prostate cancer.

In a second embodiment, the invention relates to a *Copaifera* oleoresin for use according to the first embodiment, characterized in that the oleoresin comes from the *Copaifera* species selected from the group consisting of *C. officinalis, C. multijuga, C. reticulata*.

In a third embodiment, the invention relates to the fraction of diterpenic acids and/or diterpenic acid esters of the oleoresin for use according to one of embodiments 1 or 2, characterized in that it contains at least 90 wt % diterpenic acids and/or diterpenic acid esters.

A fourth embodiment of the invention relates to a pharmaceutical composition characterized in that it contains as active agent, a *Copaifera* oleoresin according to one of embodiments 1 or 2, or a fraction according to the third embodiment, and at least one pharmaceutically acceptable excipient, for use as a medicinal product intended for the treatment and/or prevention of benign prostatic hyperplasia and/or prostate cancer. Advantageously, the oleoresin or the fraction is the only active agent in said composition.

A fifth embodiment of the invention concerns a pharmaceutical composition for use according to the fourth embodiment, characterized in that the oleoresin comes from the *Copaifera* species selected from the group consisting of *C. officinalis, C. multijuga, C. reticulata*.

A sixth embodiment of the invention concerns a pharmaceutical composition for use according to one of embodiments 4 or 5, characterized in that it contains as active agent a fraction according to the third embodiment.

A seventh embodiment of the invention also concerns a pharmaceutical composition for use according to one of embodiments 4 to 6, characterized in that it is in a form suitable for oral or intravenous administration.

Advantageously, the oleoresin or the fraction according to the present invention represents the only active principle intended for the treatment and/or prevention of benign prostatic hyperplasia and/or prostate cancer in the pharmaceutical compositions for use according to the invention.

Another embodiment of the invention relates to the use of a *Copaifera* oleoresin or a fraction as defined according to one of the preceding embodiments for the manufacture of a medicinal product intended for the treatment and/or prevention of benign prostatic hyperplasia and/or prostate cancer.

The present invention also relates to a method for the treatment and/or prevention of benign prostatic hyperplasia and/or prostate cancer comprising the administration, to an individual in need thereof, of a pharmaceutical composition comprising, or consisting of, a *Copaifera* oleoresin or a fraction according to one of the preceding embodiments, as active agent, and at least one pharmaceutically acceptable excipient.

Advantageously, according to the method of invention, the oleoresin or the fraction is the only anticancer active principle in the composition.

For the purposes of the present invention, "*Copaifera* oleoresin" means an exudate of *Copaifera* species tree(s) comprising a volatile fraction mainly composed of sesquiterpenic compounds and a non-volatile fraction mainly composed of diterpenic acids and/or diterpenic acid esters.

For the purposes of the present invention, "fraction of diterpenic acids and/or diterpenic acid esters of *Copaifera* oleoresin" means the "non-volatile" fraction of oleoresin obtained after total or partial removal, preferably total removal, of the essential oil, in particular by hydrodistillation. This non-volatile fraction contains at least 80 wt % and preferably between 80-90 wt % diterpenic acids and/or diterpenic acid esters.

The mixture of diterpenic acids and/or diterpenic acid esters can also be obtained from a *Copaifera* oleoresin, or from the "non-volatile" fraction of *Copaifera* oleoresin, in particular by liquid-liquid extraction until obtaining a mixture having a concentration of diterpenic acids and/or diterpenic acid esters between 50 and 100 wt %, particularly between 60 and 100 wt %, more particularly between 80 and 100 wt % diterpenic acids and/or diterpenic acid esters based on the total weight of the liquid fraction obtained after extraction and removal of the extraction solvent. This liquid fraction obtained after extraction and removal of the solvent represents said mixture.

The mixture of diterpenic acids and/or diterpenic acid esters comprises at least 2, or at least 3, or at least 4, or at least 4, or at least 5, or at least 6, or at least 7 diterpenic acids and/or diterpenic acid esters selected from the group consisting of: copalic acid, copaiferolic acid, agathendioic acid dimethylic ester, agathic acid, 3β-hydroxyanticopalic acid methyl ester, hardwickiic acid, 7α-acetoxyhardwickiic acid.

TABLE 1

Molecular and structural formulas and CAS number of the different diterpenic acids and/or diterpenic acid esters

| Name | Molecular formula | m/z | Structural formula |
| --- | --- | --- | --- |
| Copalic acid | $C_{20}H_{32}O_2$ | 304 | |
| Copaiferolic acid | $C_{20}H_{32}O_3$ | 320 | |
| Agathendioic acid dimethyl ester | $C_{22}H_{34}O_4$ | 362 | |
| Agathic acid | $C_{20}H_{30}O_4$ | 334 | |
| 3β-hydroxyanticopalic acid methyl ester | $C_{20}H_{30}O_4$ | 334 | |

TABLE 1-continued

Molecular and structural formulas and CAS number of the different diterpenic acids and/or diterpenic acid esters

| Name | Molecular formula | m/z | Structural formula |
|---|---|---|---|
| Hardwickiic acid | $C_{20}H_{28}O_3$ | 316 | (structure with COOH) |
| 7α-Acetoxyhardwickiic acid | $C_{22}H_{30}O_5$ | 374 | (structure, 1a: R = H) |

Preferably, the mixture of diterpenic acids and/or diterpenic acid esters includes all of the following diterpenic acids and/or diterpenic acid esters: copalic acid, copaiferolic acid, agathendioic acid dimethilic ester, agathic acid, 3β-hydroxyanticopalic acid methyl ester, hardwickiic acid, 7-alpha-acetoxyhardwickiic acid.

In an embodiment of the invention, the oleoresin comprises, in percentage by weight, between 7.5 and 40 wt % of the seven diterpenic acids and/or diterpenic acid esters mentioned above, or preferably 10 to 30 wt %.

In an embodiment the present invention, the oleoresin may be an oleoresin enriched in diterpenic acids and/or diterpenic acid esters and the content of the seven diterpenic acids and/or diterpenic acid esters of such an enriched oleoresin will be between 48 and 90 wt %, preferably between 60 and 90 wt %, preferably still between 60 and 85 wt %.

For the purposes of the present invention, the term "enriched resin" means that the oleoresin has been treated by a process designed to concentrate the content of these seven diterpenic acids and/or diterpenic acid esters in relation to the other compounds and molecules of this oleoresin. Thus, the ratios between diterpenic acids and/or diterpenic acid esters and other molecules are modified in the direction of an increase and represent different ratios of natural products or of products extracted from the tree.

TABLE 2

Mass content of the main diterpenic acids and/or diterpenic acid esters

| Name | Mass content in the oleoresin (%) | Mass content of diterpene fraction (%) |
|---|---|---|
| Copalic acid | 3 to 13 | 15 to 50 |
| Hardwickiic acid | 0.5 to 1.5 | 2 to 15 |
| Copaiferolic acid | 1 to 6 | 10 to 30 |
| Agathic acid and 3β-hydroxyanticopalic acid methyl ester | 1 to 6 | 8 to 30 |
| Agathendioic acid dimethyl ester | 1 to 6 | 10 to 30 |
| 7α-Acetoxyhardwickiic acid | 1 to 8 | 3 to 15 |

The present invention concerns *Copaifera* oleoresin for use as a medicinal product intended for the treatment and/or prevention of benign prostatic hyperplasia and/or prostate cancer.

According to a particular embodiment, the oleoresin comes from the *Copaifera* species selected from the group consisting of *Copaifera officinalis, Copaifera multijuga* or *Copaifera reticulata*, for use as a medicinal product intended for the treatment and/or prevention of benign prostatic hyperplasia and/or prostate cancer. Preferably, the oleoresin comes from the species *Copaifera officinalis*.

According to an equally advantageous embodiment of the invention, only a fraction of diterpenic acids and/or diterpenic acid esters of the oleoresin is used as a medicinal product intended for the treatment and/or prevention of benign prostatic hyperplasia and/or prostate cancer. The oleoresin fraction used consists of at least 90 wt % diterpenic acids and/or diterpenic acid esters, advantageously at least 92 wt % diterpenic acids and/or diterpenic acid esters and even more advantageously at least 95 wt % diterpenic acids and/or diterpenic acid esters.

One subject-matter of the invention concerns the use of *Copaifera* oleoresin for the manufacture of a medicinal product intended to prevent and/or treat benign prostatic hyperplasia and/or prostate cancer.

According to a preferred embodiment, the invention concerns the use of the oleoresin from *Copaifera officinalis, C. multijuga* or *C. reticulata* for the manufacture of a medicinal product intended to prevent and/or treat benign prostatic hyperplasia and/or prostate cancer.

According to a particularly preferred embodiment, the invention concerns the use of *Copaifera officinalis* oleoresin for the manufacture of a medicinal product intended to prevent and/or treat benign prostatic hyperplasia and/or prostate cancer.

According to a particular embodiment, the invention concerns the use of a fraction of diterpenic acids and/or diterpenic acid esters of *Copaifera* oleoresin, consisting of at least 90 wt % diterpenic acids and/or diterpenic acid esters, preferably at least 92 wt % diterpenic acids and/or diterpenic acid esters, and more preferably at least 95 wt % diterpenic acids and/or diterpenic acid esters, for the manufacture of a medicinal product intended to prevent and/or treat benign prostatic hyperplasia and/or prostate cancer.

According to the present invention, "treatment" means inhibition of progression, more particularly regression, preferentially disappearance of the prostatic hyperplasia or prostate tumour.

According to the present invention, "prevention" means preventing or delaying development of the hyperplasia or prostate tumour.

Treatment or prevention according to the invention means in humans or animals.

The present invention further relates to a pharmaceutical composition comprising *Copaifera* oleoresin and at least one pharmaceutically acceptable excipient.

In the present invention, "pharmaceutically acceptable" means that which is useful in the preparation of a pharmaceutical composition, which is generally safe, non-toxic and neither biologically nor otherwise undesirable and which is acceptable for human pharmaceutical use.

When used here, the term "pharmaceutically acceptable excipient" includes any adjuvant or excipient, such as solvents, solubilizers, preservatives, emulsifiers, consistency agents, spreading agents, water fixing agents, dyes, flavours, sweeteners, the use of these excipients is well known to the skilled person.

The present invention further relates to a pharmaceutical composition for use as a medicinal product.

The present invention further relates to a pharmaceutical composition characterized in that it contains as active agent a *Copaifera* oleoresin according to the invention or a fraction of diterpenic acids and/or diterpenic acid esters of *Copaifera* oleoresin according to the invention, and at least one pharmaceutically acceptable excipient, for use as a medicinal product intended for the treatment and/or prevention of benign prostatic hyperplasia and/or prostate cancer.

According to a particular embodiment of the invention, the composition contains as active agent an oleoresin from the *Copaifera* species selected from the group consisting of *C. officinalis, C. multijuga, C. reticulata* and at least one pharmaceutically acceptable excipient, for use as a medicinal product intended for the treatment and/or prevention of benign prostatic hyperplasia and/or prostate cancer.

According to another embodiment of the invention, the composition contains as active agent a fraction of diterpenic acids and/or diterpenic acid esters of the oleoresin which contains at least 90 wt % diterpenic acids and/or diterpenic acid esters, preferentially at least 92 wt % diterpenic acids and/or diterpenic acid esters and more preferably at least 95 wt % diterpenic acids and/or diterpenic acid esters and at least one pharmaceutically acceptable excipient, for use as a medicinal product intended for the treatment and/or prevention of benign prostatic hyperplasia and/or prostate cancer.

The pharmaceutical compositions according to the present invention may be formulated in a form suitable for administration to mammals, including humans. The dosage varies according to the treatment and the condition involved. These compositions are designed to be administered orally, sublingually, subcutaneously, intramuscularly, intravenously, transdermally, locally or rectally. In this case, the active ingredient may be administered in unit dosage forms, in mixture with conventional pharmaceutical carriers, to animals or humans. Appropriate unit dosage forms include oral forms such as tablets, capsules, powders, granules and oral solutions or suspensions, sublingual and buccal dosage forms, subcutaneous, topical, intramuscular, intravenous, intranasal or intraocular dosage forms and rectal dosage forms.

When a solid composition in tablet form is prepared, the main active ingredient is mixed with a pharmaceutical carrier such as gelatin, starch, lactose, magnesium stearate, talc, gum arabic, silica or similar. Tablets may be coated with sucrose or other suitable materials or treated in such a way that they have a prolonged or delayed activity and continuously release a predetermined amount of active principle.

A capsule preparation is obtained by mixing the active ingredient with a diluent and pouring the resulting mixture into soft or hard capsules.

A preparation in the form of syrup or elixir may contain the active ingredient in combination with a sweetener, an antiseptic, a flavouring agent and an appropriate dye.

Water-dispersible powders or granules may contain the active ingredient mixed with dispersing or wetting agents, or suspending agents, as well as taste correctors or sweeteners.

For rectal administration, suppositories are used that are prepared with binders that melt at rectal temperature, such as cocoa butter or polyethylene glycols.

For parenteral (intravenous, intramuscular, etc.), intranasal or intraocular administration, use is made of aqueous suspensions, isotonic saline solutions or sterile injectable solutions containing pharmacologically compatible dispersing agents and/or wetting agents.

The active principle can also be formulated as microcapsules, possibly with one or more additive carriers.

Advantageously, the pharmaceutical composition according to the present invention is in a form suitable for oral or intravenous administration.

The composition according to the present invention may be administered in combination, simultaneously, separately or sequentially, with prostatectomy, radiotherapy, and/or hormone therapy, for the treatment or prevention of prostate cancer.

The following examples illustrate the invention without limiting its scope.

EXAMPLE 1

Effects of Different Compounds on the 5α-Reductase Activity of Fibroblasts Derived from Human Follicle Dermal Papillae The objective of this study was to evaluate the potential inhibitory activity of different compounds on 5α-reductase.

Materials and Methods

The study is performed on human cells derived from donor follicle dermal papillae. This model is attractive since dermal papillae have the 5αR2 isoform as in prostate tissue. The cells are seeded in 24-well plates and cultured for 24 hours in DMEM culture medium supplemented with L-glutamine (2 mM), penicillin (50 U/ml), streptomycin (50 µg/ml) and fatal calf serum (10%) under standard culture conditions (37° C. and 5% $CO_2$). The culture medium is then replaced by a DMEM analytical medium supplemented with L-glutamine (2 mM), penicillin (50 U/ml), streptomycin (50 µg/ml) and fatal calf serum (1%). This analytical medium may contain or may not contain (control conditions) the products to be tested and a compound used as reference, finasteride (10 µM), for 24 h of pre-incubation. The cells were then treated with an analytical medium containing $[C^{14}]$-testosterone and containing or not containing (control conditions) the test or reference products, and the cells were incubated for 24 h under these conditions. After incubation, supernatants were collected for testosterone metabolism analysis. All experiments were carried out three times. The steroid molecules were extracted from the supernatants with a chloroform/methanol mixture. The organic phase was collected and the different molecular species (testosterone metabolites) were separated by thin-layer chromatography using a solvent system containing dichloromethane, ethylacetate and methanol. An autoradiography was performed on the chromatography and the transformed testosterone was estimated by densitometric analysis.

Thus, the metabolism of testosterone to dihydrotestosterone reflects the 5α-reductase activity and is evaluated by the dihydrotestosterone/testosterone ratio.

Results

A first group of experiments highlights the effects of *Copaifera officinalis* oleoresin (Table 3 below). Surprisingly, the inventors have demonstrated a significant and reproducible activity of 5α-reductase inhibition by *Copaifera officinalis* oleoresin, this inhibition even appears concentration-dependent. The strong inhibition of this enzyme by finasteride indeed validates all these experiments.

TABLE 3

Effects of *Copaifera officinalis* oleoresin and finasteride on testosterone metabolism/dihydrotestosterone production (5α-reductase activity; n = 3)

|  | Finasteride | Oleoresin (*C. officinalis*) | |
|---|---|---|---|
| Control | 10 µM | 10 µg/ml | 30 µg/ml |
| 100 | −77% | −15% | −27% |
|  | ** p < 0.01 | * p < 0.05 | ** p < 0.01 |

The statistical study is carried out versus the control group (Dunnett's test).

The oleoresin tested was prepared according to the method described in Example 2.

By way of comparison, a *Serenoa repens* extract was also tested in one of these experiments. *Serenoa repens* extract, derived from the fruit of the saw palmetto, is the phytonutrient the most studied and the most often prescribed alone or in combination, particularly in the treatment of benign prostatic hyperplasia (Gordon A E, Am. Fam. Physician, 67(06), 1281-1283, 2003). At 10 µg/ml, the *Serenoa repens* extract does not induce significant inhibition of 5α-reductase at 20 µg/ml, however, this extract induces a 23% inhibition reaching statistical significance (p<0.05 versus control).

A second series of experiments was conducted to evaluate whether the inhibitory activity on 5α-reductase was carried by the non-volatile fraction or rather by the volatile fraction corresponding to the essential oil. The results are summarized in Table 4 below. The preparation of the volatile and non-volatile fractions is carried out according to the method described in Example 4 with the diethyl ester as apolar solvent.

TABLE 4

Effects of non-volatile and volatile fractions from *Copaifera officinalis* oleoresin on testosterone metabolism/dihydrotestosterone production (5α-reductase activity)

|  | Non-volatile fraction | | | Volatile fraction | |
|---|---|---|---|---|---|
| Control | 0.3 µg/ml | 1 µg/ml | 3 µg/ml | 7.7 µg/ml | 23.1 µg/ml |
| 100 | 0 | −6% | −14% | +2% | +9% |
|  | p = NS | p = NS | * p < 0.05 | p = NS | p = NS |

The statistical study is carried out versus the control group (Dunnett's test).

It turns out that the activity of *Copaifera officinalis* oleoresin is carried by the non-volatile fraction, indeed no activity of the volatile fraction was detected. Inhibition of 5α-reductase is only 14% with the non-volatile fraction, but this reduction reaches statistical significance (p<0.05).

A third series of experiments was carried out to show that other *Copaifera species*, in particular *C. multijuga*, also had an advantageous activity on 5α-reductase inhibition. The inventors focused on the non-volatile fraction, which carries the inhibitory activity. The results are summarized in Table 5 below.

TABLE 5

Effects of non-volatile fractions from *Copaifera multijuga* oleoresin on testosterone metabolism/dihydrotestosterone production (5α-reductase activity; n = 2)

|  | Non-volatile fraction *Copaifera multijuga* | |
|---|---|---|
| Control | 1 µg/ml | 10 µg/ml |
| 100 | 0 | −31% |
|  | p = NS | ** p < 0.01 |

The statistical study is carried out versus the control group (Dunnett's test).

The preparation of the volatile and non-volatile fractions is carried out according to the method described in Example 4 with the diethyl ester as apolar solvent.

These results clearly show that several *Copaifera* species are of interest. Indeed, the non-volatile fraction of the species *C. multijuga* reaches 31% inhibition of 5α-reductase at 10 µg/ml.

All these results lead to the conclusion that *Copaifera* oleoresin has an extremely advantageous inhibitory activity on 5α-reductase. This activity is carried by the non-volatile fraction of the oleoresin. Finally, the inventors have also shown that this activity is found on several *Copaifera* species.

EXAMPLE 2

Preparation of Oleoresin

The trunk bark of *Copaifera officinalis* and/or *Copaifera multijuga* and/or *Copaifera reticulata* trees is notched to recover the oleoresin. This is then homogenized and stabilized under nitrogen. The active substance is 100% raw oleoresin from the trunk of *Copaifera officinalis* and/or *Copaifera multijuga* and/or *Copaifera reticulata*.

LCMS analysis of a *Copaifera officinalis* oleoresin

Each sample was analysed by UHPLC-QTOFMS using a conventional linear gradient.

Separation on a Waters Acquity UHPLC system.
Column 100×2.1 mm, 1.7 μm, Acquity BEH C18 equipped with a pre-column
Mobile phase:
Mobile phase A: LCMS grade water +0.1% formic acid
Mobile phase B: LCMS grade acetonitrile +0.1% formic acid
Gradient:

| Time (min) | % A | % B |
|---|---|---|
| 0-0.5 | 50 | 50 |
| 0.5-4 | 50→40 | 50→60 |
| 4-12 | 40→1 | 60→99 |
| 12-15 | 1 | 99 |
| 15-15.5 | 1→50 | 99→50 |
| 15.5-19 | 50 | 50 |

Acquisitions:
UV 220 nm

| Structure | m/z | Content in the oleoresin (weight % relative to the weight of oleoresin) |
|---|---|---|
| Copalic acid | 304 | 5.69 |
| Hardwickiic acid | 316 | 0.61 |
| Copaiferolic acid | 320 | 2.90 |
| Agathic acid and 3β-hydroxyanticopalic acid methyl ester | 334 | 2.35 |
| Agathendioic acid dimethyl ester | 362 | 2.92 |
| 7α-Acetoxyhardwickiic acid | 374 | 0.79 |

EXAMPLE 3

Preparation of the Non-Volatile Fraction

The oleoresin obtained according to Example 2 is suspended in 10 volumes of water heated to 100° C. for 4 h to make a hydrodistillation. The volatile essential oil is recovered by condensation. After hydrodistillation, the distillation residue is recovered. After drying by lyophilization or other drying means, the residue constitutes the non-volatile fraction.

EXAMPLE 4

Alternative Preparation of the Non-Volatile Fraction

A volume of *Copaifera* oleoresin obtained according to Example 2 is diluted in 8 to 10 volumes of a water-immiscible lipophilic solvent (such as diethyl ether, ethyl acetate). This solution is extracted by liquid/liquid extraction with a 5% sodium hydroxide (NaOH) solution. The operation is repeated 3 times with 4 to 5 volumes of 5% NaOH. The lower phase (basic aqueous phase) is acidified by the addition of 1 N hydrochloric acid (HCl) and then extracted by liquid/liquid extraction with a water-immiscible apolar solvent (such as diethyl ether, ethyl acetate). The ethyl acetate phase is washed with water and then dried over Na2SO4.

After removal of the solvent by rotavapor or other drying means, the dry residue obtained corresponds to the mixture of diterpenic acids and/or diterpenic acid esters according to the invention.

| Structure | m/z | Weight content in the non-volatile fraction |
|---|---|---|
| Copalic acid | 304 | 28.45 |
| Hardwickiic acid | 316 | 3.05 |
| Copaiferolic acid | 320 | 14.52 |
| Agathic acid and 3β-hydroxyanticopalic acid methyl ester | 334 | 11.77 |
| Agathendioic acid dimethyl ester | 362 | 14.58 |
| 7α-Acetoxyhardwickiic acid | 374 | 3.96 |

The invention claimed is:

1. A method for treating benign prostatic hyperplasia which comprises administering a therapeutically effective amount of a *Copaifera* oleoresin to a human or animal in need thereof to effectively treat the benign prostatic hyperplasia in the human or animal in need thereof.

2. The method of claim 1, wherein the *Copaifera* is selected from the group consisting of *Copaifera officinalis*, *Copaifera multijuga*, and *Copaifera reticulata*.

3. The method of claim 1, wherein the oleoresin comprises a fraction of diterpenic acids and/or diterpenic acid esters and wherein the fraction contains at least 90 wt. % diterpenic acids and/or diterpenic acid esters.

4. A method for treating benign prostatic hyperplasia in a human or animal in need thereof comprising administering to the human or animal in need thereof a therapeutically effective amount of a pharmaceutical composition comprising:
   a *Copaifera* oleoresin or a *Copaifera* oleoresin fraction, wherein said fraction comprises at least 90 wt. % diterpenic acids and/or diterpenic acid esters, and
   at least one pharmaceutically acceptable excipient,
   to effectively treat the benign prostatic hyperplasia in the human or animal in need thereof.

5. The method of claim 4, wherein the *Copaifera* is selected from the group consisting of *Copaifera officinalis*, *Copaifera multijuga*, and *Copaifera reticulata*.

6. The method of claim 4, wherein the pharmaceutical composition is administered orally or intravenously to the human or animal in need thereof.

* * * * *